United States Patent
Kagami et al.

(10) Patent No.: US 8,153,692 B2
(45) Date of Patent: Apr. 10, 2012

(54) ORAL PREPARATION FOR PREVENTING OR IMPROVING SKIN DRYNESS

(75) Inventors: Erika Kagami, Tsukuba (JP); Koji Morishita, Tsukuba (JP)

(73) Assignee: Kyowa Hakko Bio Co., Ltd., Tokyo (JP)

( * ) Notice: Subject to any disclaimer, the term of this patent is extended or adjusted under 35 U.S.C. 154(b) by 100 days.

(21) Appl. No.: 12/096,347

(22) PCT Filed: Dec. 5, 2006

(86) PCT No.: PCT/JP2006/324231
§ 371 (c)(1),
(2), (4) Date: Aug. 11, 2008

(87) PCT Pub. No.: WO2007/066642
PCT Pub. Date: Jun. 14, 2007

(65) Prior Publication Data
US 2010/0004335 A1 Jan. 7, 2010

(30) Foreign Application Priority Data
Dec. 5, 2005 (JP) .................................. 2005-350816

(51) Int. Cl.
*A61K 31/195* (2006.01)
(52) U.S. Cl. ........................................................ 514/564
(58) Field of Classification Search ................... 514/564
See application file for complete search history.

(56) References Cited

U.S. PATENT DOCUMENTS

| 5,702,688 A * | 12/1997 | Yu et al. ........................ 424/59 |
| 2004/0191205 A1 | 9/2004 | Evans et al. |
| 2007/0218150 A1 | 9/2007 | Akashi et al. |

FOREIGN PATENT DOCUMENTS

| CN | 1451426 A | 10/2003 |
| JP | 9-505822 A | 6/1997 |
| JP | 2005-306831 A | 4/2005 |
| WO | WO 95/15147 A1 | 6/1995 |
| WO | WO 2004/082654 A1 | 9/2004 |
| WO | WO 2005/105126 A1 | 11/2005 |

OTHER PUBLICATIONS

Horikawa et al., *Fragrance Journal*, 10: 29-32 (1999).
Jacobson et al., *The Journal of Investigative Dermatology*, 95(3): 296-300 (1990).
Koyama et al., *J. Soc. Cosmet. Chem.*, 35(4): 183-195 (Jul. 1984).
Watanabe et al., *Archives of Dermatology*, 127: 1689-1692 (Nov. 1991).

* cited by examiner

*Primary Examiner* — Raymond Henley, III
(74) *Attorney, Agent, or Firm* — Leydig, Voit & Mayer, Ltd.

(57) ABSTRACT

An oral preparation for the prophylaxis or improvement of dry skin accompanied by atopic dermatitis, xeroderma, chapped hand, chapped skin and the like is provided. The present invention can provide an oral preparation for the prophylaxis or improvement of dry skin, which comprises citrulline or a salt thereof as an active ingredient.

3 Claims, 1 Drawing Sheet

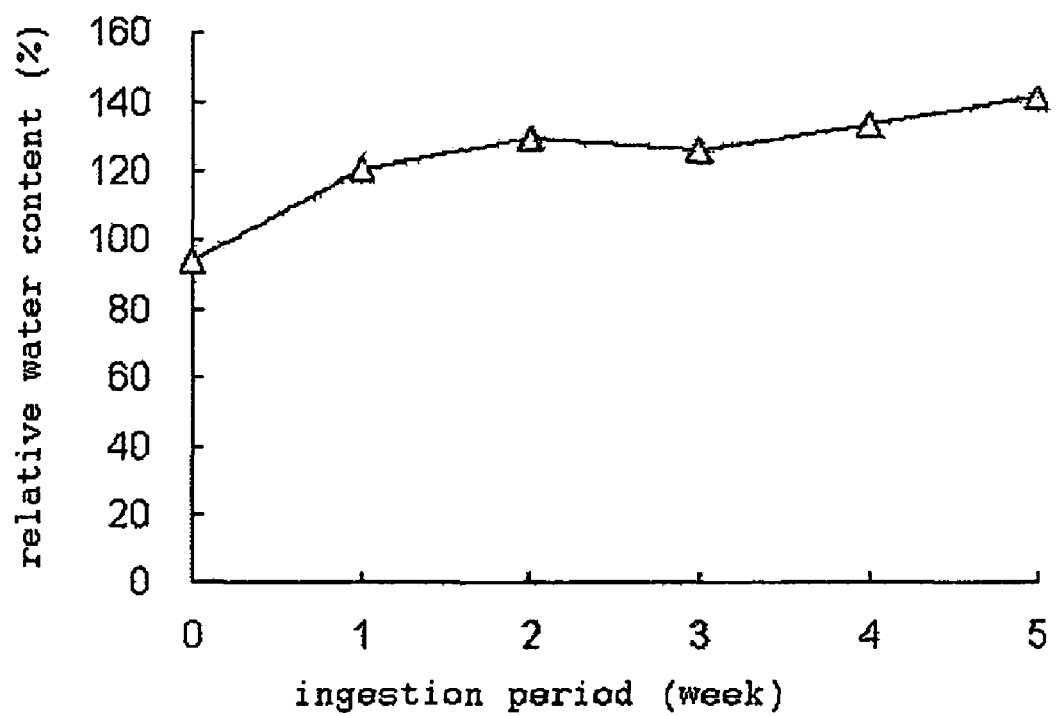

ORAL PREPARATION FOR PREVENTING OR IMPROVING SKIN DRYNESS

TECHNICAL FIELD

The present invention relates to oral preparations for the prophylaxis or improvement of dry skin, which comprise citrulline or a salt thereof as an active ingredient.

BACKGROUND ART

The skin is always exposed to various irritations from the external environment. The stratum corneum of the skin has barrier functions of preventing invasion of these irritations or foreign matters from the outside and preventing transpiration of water within the body. It has been known that water content in the stratum corneum of the skin of persons or animals in which such barrier functions are reduced is decreased. For example, it has been reported that the water content in the stratum corneum of the skin is decreased in patients with atopic dermatitis (refer to Non-patent Document 1) or with aging (refer to Non-patent Document 2).

As a method for maintaining or improving moistening property of the skin, a method in which the barrier functions of the stratum corneum are supplemented with a blocking agent such as a vaseline ointment or a water-in-oil emulsion, a method in which the water content of the stratum corneum is supplemented with a moistening agent such as sorbitol or glycerin, a method in which skin inflammation is suppressed with an antiinflammatory agent such as glycyrrhizic acid, a method in which skin cells are activated with, for example, vitamins or hormones, and the like have been so far used (refer to Non-patent Document 3).

Citrulline is known to be a constituent of NMF (natural moisturizing factor), which is an epidermal moisturizing component (see non-patent reference 4). It has been reported that a topical administration of Citrulline in combination with arginine, ornithine etc. can prevent or treat nerve sensory symptoms such as atopic skin and the like (patent reference 1). However, it is not known that oral ingestion of citrulline or a salt thereof can prevent or improve a dry state of the skin.

Patent Document 1: Japanese Translation No.505822/1997 of PCT Application
Non-Patent Document 1: "Archives of Dermatology", 1991, vol. 127, p. 1689
Non-Patent Document 2: "Journal of Investigative Dermatology", 1990, vol. 95, p. 296
Non-Patent Document 3: "Fragrance Journal", 1999, vol. 10, p. 29
Non-Patent Document 4: "Journal of the Society of Cosmetic Chemists", 1984, vol. 35, p. 183

DISCLOSURE OF THE INVENTION

Problems to be Solved by the Invention

An object of the invention is to provide oral preparations for the prophylaxis or improvement of dry skin.

Means for Solving the Problems

The present invention relates to the following (1) to (3).
(1) An oral preparation for the prophylaxis or improvement of dry skin, which comprises citrulline or a salt thereof as an active ingredient.
(2) A method for preventing or improving dry skin, which comprises orally administering an effective amount of citrulline or a salt thereof to a subject in need thereof.
(3) Use of citrulline or a salt thereof for the manufacture of an oral preparation for the prophylaxis or improvement of dry skin.

EFFECT OF THE INVENTION

The present invention can provide safe and effective oral preparations for the prophylaxis or improvement of dry skin.

BRIEF DESCRIPTION OF THE DRAWING

FIG. 1 is a graph showing a change in relative epidermal water content with time. The ordinate of the graph represents a relative epidermal water content, and the abscissa of the graph represents an ingestion period of citrulline.

BEST MODE FOR CARRYING OUT THE INVENTION

Examples of citrulline to be used in the present invention include L-citrulline and D-citrulline, with preference given to L-citrulline.

Citrulline can be obtained by chemical synthesis, fermentation and the like. In addition, citrulline can also be obtained by purchasing a commercially available product.

As a method for chemically synthesizing citrulline, for example, the methods described in J. Biol. Chem. 122, 477 (1938) and J. Org. Chem. 6, 410 (1941) can be mentioned.

As a method for producing L-citrulline by fermentation, for example, the methods described in Japanese Published Unexamined Patent Application Nos. 075387/1978 and 068091/1988 can be mentioned.

In addition, L-citrulline and D-citrulline can also be purchased from Sigma-Aldrich Co. Ltd. and the like.

Examples of the salts of citrulline include acid addition salts, metal salts, ammonium salts, organic amine addition salts, amino acid addition salts and the like.

Examples of the acid addition salt include inorganic acid salts such as hydrochloride, sulfate, nitrate salt, phosphate and the like, and organic acid salts such as acetate, maleate, fumarate, citrate, malate, lactate, α-ketoglutarate, gluconate, caprylate and the like.

Examples of the metal salt include alkali metal salts such as sodium salt, potassium salt and the like, alkaline earth metal salts such as magnesium salt, calcium salt and the like, aluminum salt, zinc salt and the like.

Examples of the ammonium salt include salts with ammonium, tetramethylammonium and the like.

Examples of the organic amine addition salt include salts with morpholine, piperidine and the like.

Examples of the amino acid addition salt include salts with glycine, phenylalanine, lysine, aspartic acid, glutamic acid and the like.

Among the above-mentioned salts of citrulline, malate is preferably used. Other salts or two or more salts may be used in an appropriate combination.

The oral preparation for the prophylaxis or improvement of dry skin of the present invention can contain, in addition to citrulline or a salt thereof, additives suitable for each use as appropriate.

Since the water content of the skin increases by administration or ingestion of the oral preparation for the prophylaxis or improvement of dry skin of the present invention, a dry state of the skin can be prevented or improved.

The dry state of the skin includes a dry state of the skin accompanied by atopic dermatitis, xeroderma, chapped hand, chapped skin or the like.

The chapped skin refers to a symptom that the stratum corneum is roughened by drying and a moist feeling is lost when the surface of the skin is touched.

The chapped hand refers to a symptom caused by irritating the hand when a person whose skin is easily dried constitutionally because of less keratin intracellular lipid or the like does scrubbing and washing such as kitchen work or laundering or repeatedly uses chemicals such as a shampoo and a hair dye.

The oral preparation for the prophylaxis or improvement of dry skin of the present invention contains citrulline or a salt thereof and may contain one or more pharmaceutically acceptable carriers as required and also active ingredients for another treatment as required.

The oral preparation for the prophylaxis or improvement of dry skin of the present invention can be prepared by mixing citrulline or a salt thereof with the carriers as required and then subjecting the mixture to any method well-known in the technical field of pharmaceutics.

When the oral preparation for the prophylaxis or improvement of dry skin of the present invention is formulated, additives such as excipients, binders, disintegrators, lubricants, dispersing agents, suspending agents, emulsifiers, diluents, buffers, antioxidants and anti-bacterial agents can be used.

Examples of the dosage form of the oral preparation for the prophylaxis or improvement of dry skin include tablets, powders, granules, emulsions, syrups, capsules and the like.

For example, when the dosage form is tablets, powders, granules or the like, the formulation can be conducted by adding saccharides such as lactose, white soft sugar, glucose, sucrose, mannitol and sorbitol, starches such as potato starch, wheat starch and corn starch, inorganic substances such as calcium carbonate, calcium sulfate, sodium hydrogencarbonate and sodium chloride, excipients, for example, powdered plants such as powdered glycyrrhiza and powdered gentian, disintegrators such as starch, agar, gelatin powder, crystalline cellulose, carmellose sodium, carmellose calcium, calcium carbonate, sodium hydrogencarbonate and sodium alginate, lubricants such as magnesium stearate, talc, hydrogenated vegetable oil, macrogol and silicone oil, binders such as polyvinyl alcohol, hydroxypropyl cellulose, methyl cellulose, ethyl cellulose, carmellose, gelatin and starch paste solution, surfactants such as fatty acid esters, plasticizers such as glycerin, and the like.

When the dosage form is a liquid preparation such as syrup, formulation can be conducted by adding water, saccharides such as sucrose, sorbitol and fructose, glycols such as polyethylene glycol and propylene glycol, oils such as sesame oil, olive oil and soybean oil, antiseptics such as p-hydroxybenzoic acid ester, flavors such as strawberry flavor and peppermint, and the like.

Moreover, the preparation suitable for oral administration may also contain food additives which are generally used in foods and drinks, such as sweeteners, coloring agents, preservatives, thickening stabilizers, antioxidants, color-developing agents, bleaching agents, fungicides, gum bases, bitter agents, enzymes, brightening agents, sour agents, seasonings, emulsifier, nutrient supplements, additional materials for preparation, flavors and spice extracts. The preparation suitable for oral administration may be used as foods and drinks (e.g., health food, functional food, food supplement, specified health food and the like) for the prophylaxis or improvement of dry skin, directly or in the form of, for example, powdered food, sheet food, bottled food, canned food, retort food, capsule food, tablet food, liquid food, health drink and the like.

The concentration of citrulline or a salt thereof in the oral preparation for the prophylaxis or improvement of dry skin of the present invention is properly selected according to the type of the oral preparation, the effect to be expected by administration of the oral preparation and the like. It is usually 0.1 to 90% by weight, preferably 0.5 to 70% by weight, especially preferably 1 to 50% by weight as citrulline or a salt thereof.

The dose of the oral preparation for the prophylaxis or improvement of dry skin of the present invention may vary depending upon the dosage form, and the age and weight of a person to which the agent is being administered, and the like. It is usually 100 to 10,000 mg, preferably 100 to 2,000 mg, especially preferably 200 to 1,000 mg a day for an adult patient as citrulline or a salt thereof. The oral preparation is administered once or in several divided portions a day. Although the administration period is not particularly limited, it is usually one day to one year, preferably one week to three months.

Test Examples are described below in which an effect of increase in skin water content by oral ingestion of citrulline were examined.

TEST EXAMPLE 1

HOS:HR-1 mice (male, 5 weeks old, purchased from Charles River Co., Ltd.) were used in the test. The breeding conditions were that the room temperature was 22±2° C., the humidity was 35±15% and a feed and water were freely ingested.

Each test group consisted of 10 mice. A commercially available powder feed CE-2 (manufactured by Clea Japan) was fed to mice of the first group, CE-2 containing 1.0% by weight of L-citrulline (manufactured by Kyowa Hakko Kogyo Co., Ltd.) was fed to mice of the second group.

The water content of the skin surface on the back thigh upper portion of each mouse was measured with SKICON-200 (manufactured by IBS) every one week, from a week to five weeks after the start-up of the feeding of each feed. The measurement was conducted ten times for each mouse, and an average value of each mouse was obtained. Further, an average value of each test group was calculated.

The relative epidermal water content was calculated according to the following formula using the average value.

Relative epidermal water content (%)=($A2/A1$)×100

A1: Epidermal water content of the first group
A2: Epidermal water content of the second group The results are shown in FIG. 1.

From FIG. 1, it became clear that the water content of the skin is markedly improved by the oral ingestion of citrulline.

EXAMPLE 1

Production of Tablets Containing Citrulline

Tablets containing citrulline are produced by an ordinary method. That is, the following components are uniformly mixed, and the mixture is tableted with a single punch tableting machine to obtain tablets each having a diameter of 5 mm and a weight of 15 mg.

| Components | Amount |
| --- | --- |
| L-citrulline | 10.0 g |
| lactose | 90.0 g |
| dry corn starch | 2.0 g |
| talc | 1.8 g |
| magnesium stearate | 0.2 g |

EXAMPLE 2

Production of Granules Containing Citrulline

The tablets obtained in Example 1 are milled, granulated and sieved to obtain granules of 20 to 50 mesh.

EXAMPLE 3

Production of a Drink Containing Citrulline

A drink containing citrulline is produced by uniformly stirring and dissolving the following components and adding purified water to adjust the total volume to 1,000 ml. A suitable amount of a flavor or a pigment in the following components refers to an amount which is ordinarily used in the production of drinks, and a suitable amount of purified water refers to an amount required for adjusting the total volume to 1,000 ml by addition to other components.

| Components | Amount |
| --- | --- |
| L-citrulline | 5.0 g |
| sodium benzoate | 1.0 g |
| fructose | 10.0 g |
| flavor | suitable amount |
| pigment | suitable amount |
| purified water | suitable amount |

EXAMPLE 4

Production of Candies Containing Citrulline citrulline-containing candies comprising the following components are produced by an ordinary method.

| Components | Amount |
| --- | --- |
| L-citrulline | 1.00 g |
| sorbitol powder | 98.75 g |
| flavor | 0.20 g |
| sorbitol seed | 0.05 g |

EXAMPLE 5

Production of a Feed Containing Citrulline

A citrulline-containing animal feed comprising the following components is produced by an ordinary method.

| Components | Amount |
| --- | --- |
| L-citrulline | 1.0 g |
| lard | 5.0 g |
| corn oil | 1.0 g |
| sucrose | 20.0 g |
| cellulose | 5.0 g |
| choline chloride | 0.2 g |
| vitamin mixture | 1.0 g |
| mineral mixture | 3.5 g |
| corn starch | 44.3 g |

Industrial Applicability

The present invention can provide safe and effective oral preparations for the prophylaxis or improvement of dry skin.

The invention claimed is:

1. An oral preparation for increasing skin water content, which comprises citrulline or a salt thereof as the sole active ingredient, wherein the oral preparation is selected from the group consisting of a drink, tablet, powder, granule, emulsion, syrup, and capsule.

2. A method for increasing skin water content, which comprises orally administering an effective amount of citrulline or a salt thereof as the sole active ingredient in the form of an oral preparation selected from the group consisting of a drink, tablet, powder, granule, emulsion, syrup, and capsule to a subject in need thereof.

3. A method of preparing an oral preparation, which method comprises formulating citrulline or a salt thereof as the sole active ingredient with one or more pharmaceutically acceptable carriers to provide an oral preparation for increasing skin water content in a subject that ingests the oral preparation, wherein the oral preparation is selected from the group consisting of a drink, tablet, powder, granule, emulsion, syrup, and capsule.

* * * * *